US009080948B2

(12) United States Patent
Sun et al.

(10) Patent No.: US 9,080,948 B2
(45) Date of Patent: Jul. 14, 2015

(54) DYNAMIC PEAK TRACKING IN X-RAY PHOTOELECTRON SPECTROSCOPY MEASUREMENT TOOL

(71) Applicant: International Business Machines Corporation, Armonk, NY (US)

(72) Inventors: Bing Sun, Tarrytown, NY (US); Min Dai, Mahwah, NJ (US); Srinivasan Rangarajan, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 126 days.

(21) Appl. No.: 13/826,316

(22) Filed: Mar. 14, 2013

(65) Prior Publication Data

US 2014/0264015 A1     Sep. 18, 2014

(51) Int. Cl.
*G21K 7/00*     (2006.01)
*G01N 23/227*   (2006.01)

(52) U.S. Cl.
CPC .... *G01N 23/2273* (2013.01); *G01N 2223/6113* (2013.01)

(58) Field of Classification Search
None
See application file for complete search history.

(56) References Cited

U.S. PATENT DOCUMENTS

| | | | | |
|---|---|---|---|---|
| 5,352,894 A * | 10/1994 | Yasuo | ............................ | 250/305 |
| 6,720,556 B2 * | 4/2004 | Cohen et al. | ...................... | 850/9 |
| 6,800,852 B2 * | 10/2004 | Larson et al. | ................. | 250/305 |
| 6,891,158 B2 * | 5/2005 | Larson et al. | ................. | 250/305 |
| 7,231,324 B2 * | 6/2007 | Orrock et al. | ................. | 702/189 |
| 7,359,487 B1 * | 4/2008 | Newcome | ...................... | 378/143 |
| 7,399,963 B2 * | 7/2008 | Schueler et al. | ............. | 250/305 |
| 7,411,188 B2 * | 8/2008 | deCecco et al. | ............. | 250/305 |
| 7,420,163 B2 * | 9/2008 | Schueler | ....................... | 250/305 |
| 7,449,682 B2 * | 11/2008 | Larson et al. | ................. | 250/281 |
| 7,456,399 B1 * | 11/2008 | Soderstrom | ................... | 250/305 |
| 7,561,438 B1 * | 7/2009 | Liu | .............................. | 361/766 |
| 7,720,631 B2 * | 5/2010 | Pike | ............................. | 702/152 |
| 7,884,321 B2 * | 2/2011 | deCecco et al. | ............. | 250/305 |
| 7,996,178 B2 * | 8/2011 | Pike | ............................. | 702/152 |
| 8,011,830 B2 * | 9/2011 | Schueler et al. | ............. | 378/207 |
| 8,269,167 B2 * | 9/2012 | deCecco et al. | ............. | 250/305 |
| 2002/0020814 A1 * | 2/2002 | Cohen et al. | .................. | 250/306 |

* cited by examiner

*Primary Examiner* — Andrew Smyth
(74) *Attorney, Agent, or Firm* — Catherine Ivers; Howard M. Cohn

(57) ABSTRACT

Systems and methods for performing X-ray Photoelectron Spectroscopy (XPS) measurements in a semiconductor environment are disclosed. A reference element peak is selected and tracked as part of the measurement process. Peak shift of the reference element peak, in electron volts (eV) is tracked and applied to other portions of acquired spectrum to compensate for the shift, which results from surface charge fluctuation.

16 Claims, 8 Drawing Sheets

DYNAMIC PEAK TRACKING IN X-RAY PHOTOELECTRON SPECTROSCOPY MEASUREMENT TOOL

FIELD OF THE INVENTION

The present invention relates generally to measurement techniques, and more particularly, to measurement techniques for X-ray photoelectron spectroscopy.

BACKGROUND OF THE INVENTION

Integrated circuits (ICs) are formed on semiconductor substrates such as wafers. The formation of the integrated circuits may include numerous processing steps such as deposition of various layers, etching some of the layers, and multiple furnace treatments. The integrated circuits are then separated into individual dies, which are packaged and attached to circuit boards.

During the various processing steps involved in the creation of the integrated circuits, various layers of different materials, such as conductors, dielectrics, and semiconductors, are formed on the surface of the wafer where the integrated circuits are being formed. The manufacturers of the integrated circuits often test the composition of the various layers to ensure that the proper materials are being deposited on the substrates.

Characterization of these layers can be performed using various techniques such as X-ray Photoelectron Spectroscopy (XPS). X-rays are used in XPS as the primary radiation to excite the emission of photoelectrons from the wafer surface. The energy of these electrons are representative of the elemental bonding state in the surface of the wafer, and their intensity can be used for compositional and thickness analysis. The various films used to fabricate a modern semiconductor device can have very narrow tolerances in order to achieve an acceptable yield. Hence, it is desirable to have improvements in metrology used for assessing the effectiveness of semiconductor manufacturing processes.

SUMMARY OF THE INVENTION

In one embodiment, a method for performing measurements with an X-ray photoelectron spectroscopy measurement tool is provided, comprising irradiating a semiconductor substrate with X-ray energy, detecting emitted electrons from the semiconductor substrate, selecting a reference element peak based on the detected emitted electrons, recording an initial location for the reference element peak, computing a shift in location for the reference element peak, and applying a correction to a plurality of element windows, based on the computed shift.

In another embodiment, a system for performing measurements with an X-ray photoelectron spectroscopy measurement tool is provided, comprising an X-ray source configured and disposed to irradiate a semiconductor substrate, a detector configured to detect emitted electrons from the semiconductor substrate, a processor, configured and disposed to access a non-transitory memory, wherein the non-transitory memory contains instructions, that when executed by the processor, perform the steps of selecting a reference element peak based on the emitted electrons, recording an initial location for the reference element peak, computing a shift in location for the reference element peak; and applying a correction to a plurality of element windows, based on the computed shift.

In another embodiment, a non-transitory computer-readable medium is provided, comprising instructions, which when executed by a processor, perform the steps of irradiating a semiconductor substrate with X-ray energy, detecting emitted electrons from the semiconductor substrate, selecting a reference element peak based on the detected emitted electrons, recording an initial location for the reference element peak, computing a shift in location for the reference element peak, and applying a correction to a plurality of element windows, based on the computed shift.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1A:
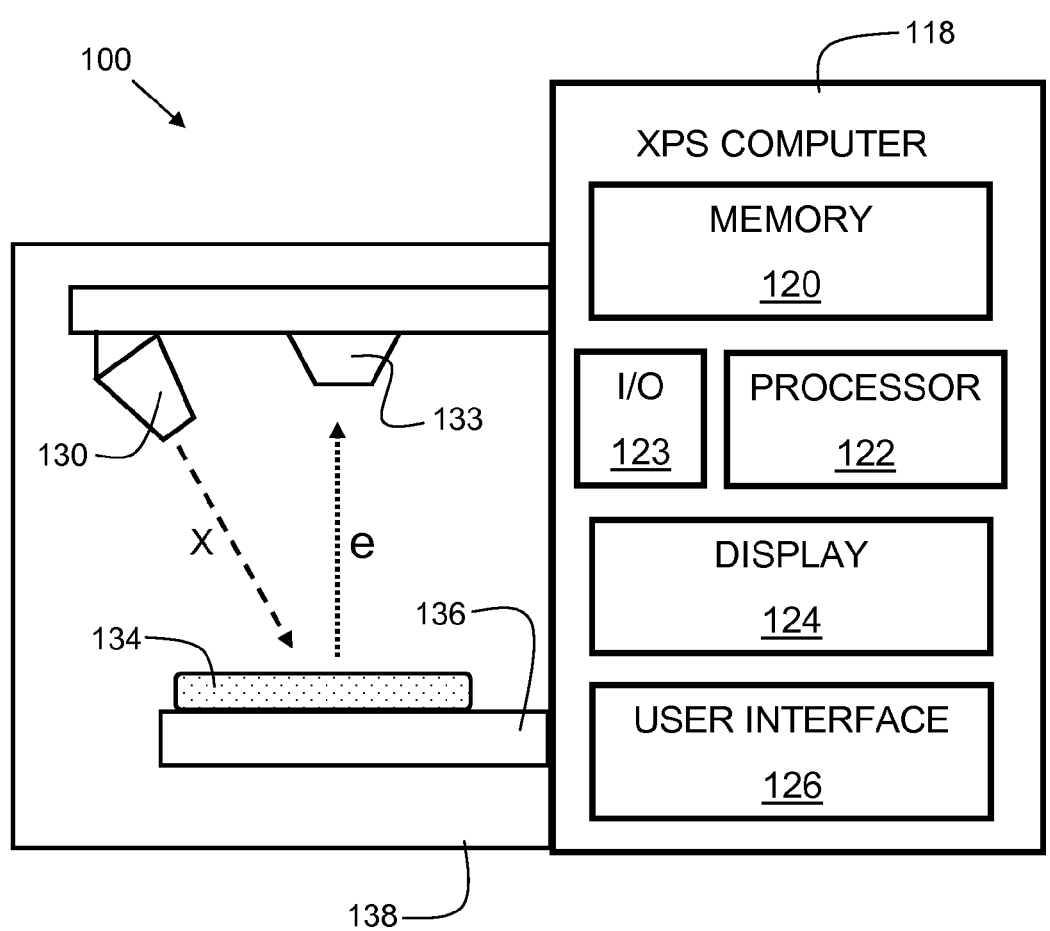

Often, similar elements may be referred to by similar numbers in various figures (FIGs) of the drawing, in which case typically the last two significant digits may be the same, the most significant digit being the number of the drawing figure (FIG). Furthermore, for clarity, some reference numbers may be omitted in certain drawings.

FIG. 1A is a block diagram of a system in accordance with embodiments of the present invention.

Figure 1B:
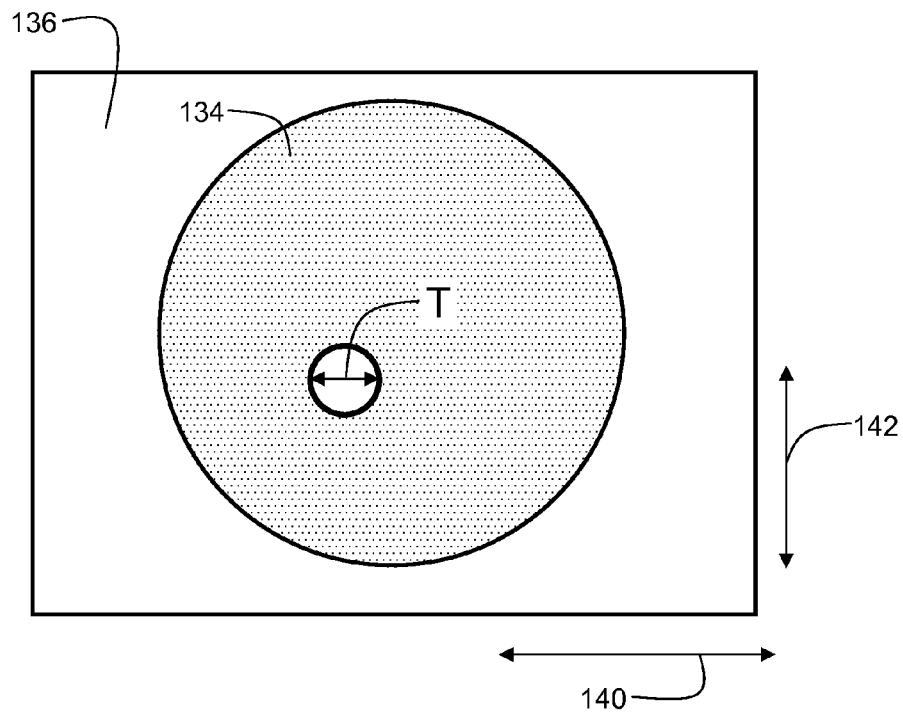

FIG. 1B is a top-down view of a semiconductor substrate indicating a target area.

Figure 2:
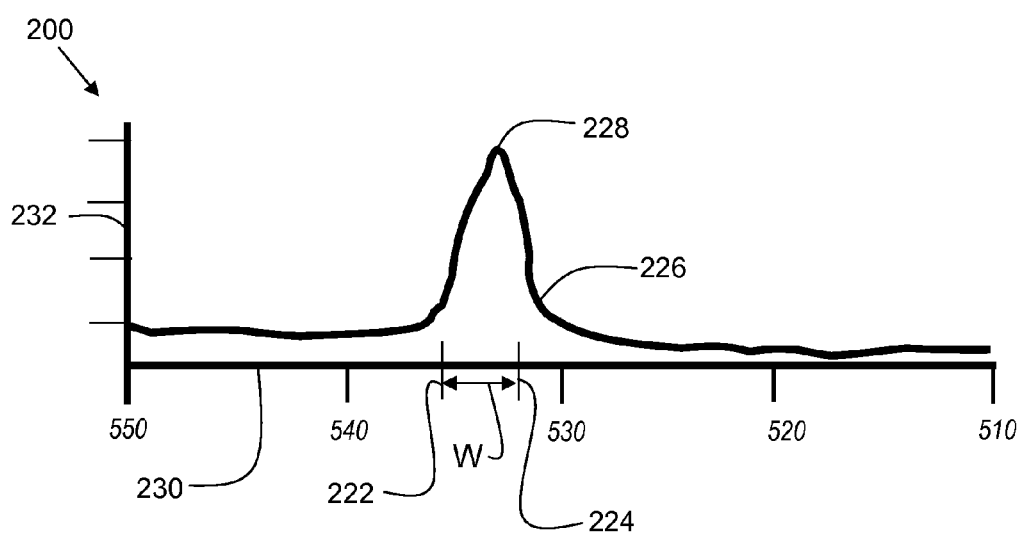

FIG. 2 is a graph of an exemplary XPS reference element peak.

Figure 3A:
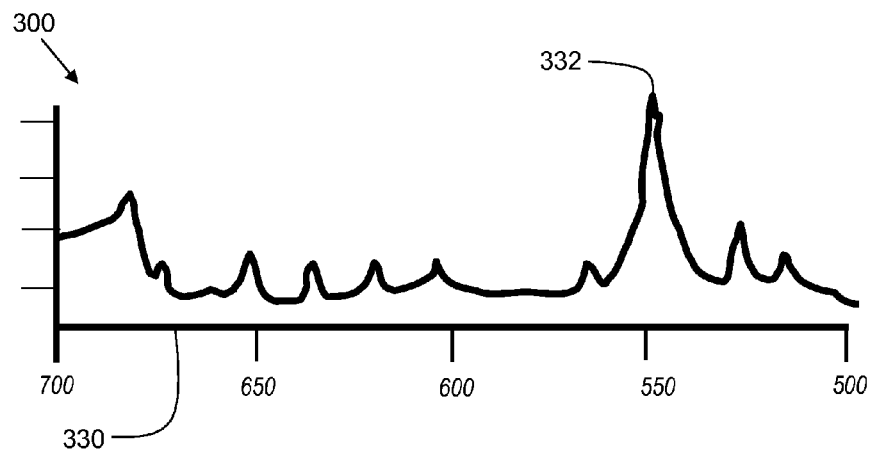

FIG. 3A shows an exemplary pre-scan spectrum.

Figure 3B:
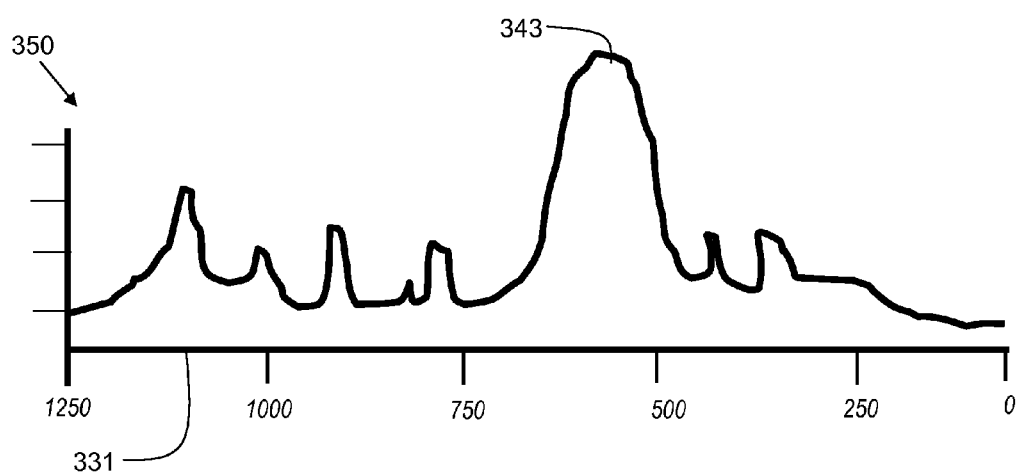

FIG. 3B shows another exemplary pre-scan spectrum.

Figure 4:
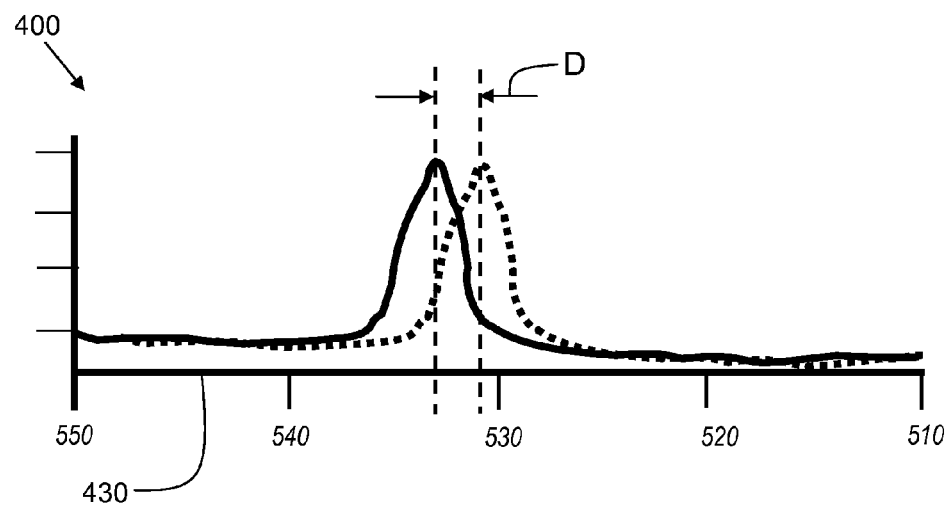

FIG. 4 is a graph illustrating reference element peak shift.

Figure 5:
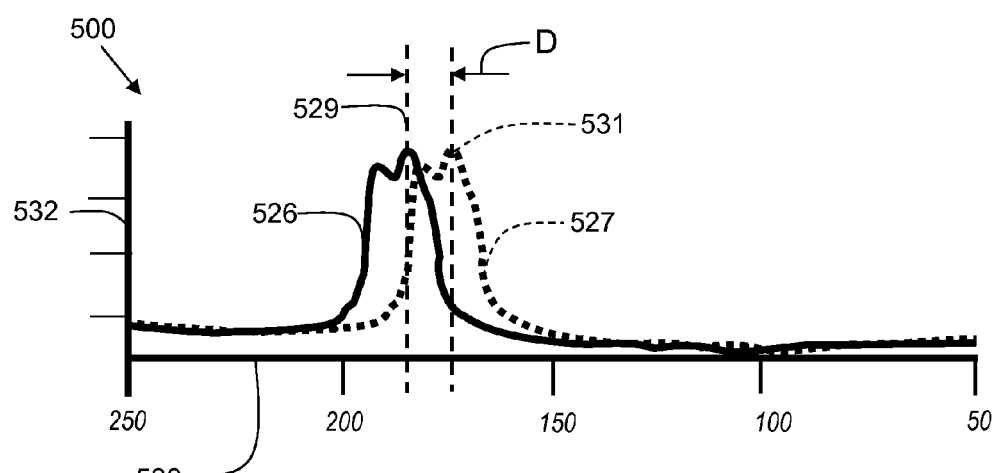

FIG. 5 is a graph of exemplary XPS measurement spectra, indicating shift.

Figure 6:
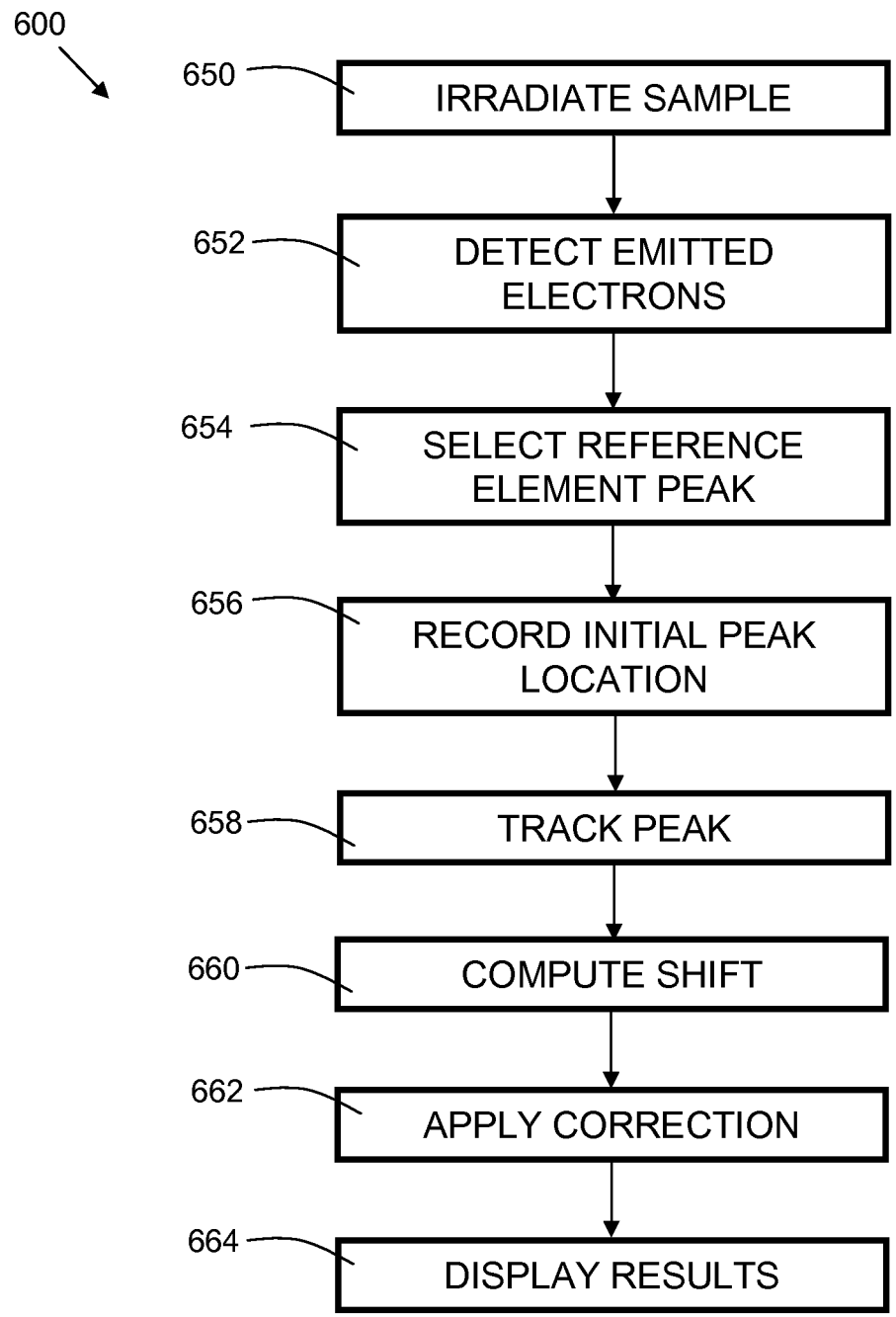

FIG. 6 is a flowchart indicating process steps for embodiments of the present invention.

Figure 7:
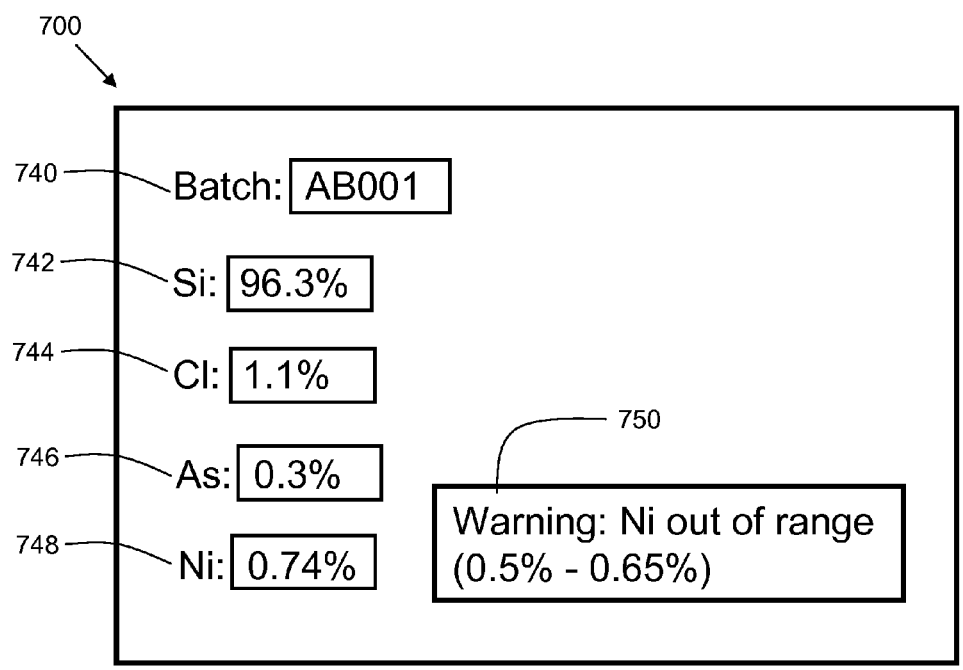

FIG. 7 shows an exemplary display in accordance with embodiments of the present invention.

Figure 8:
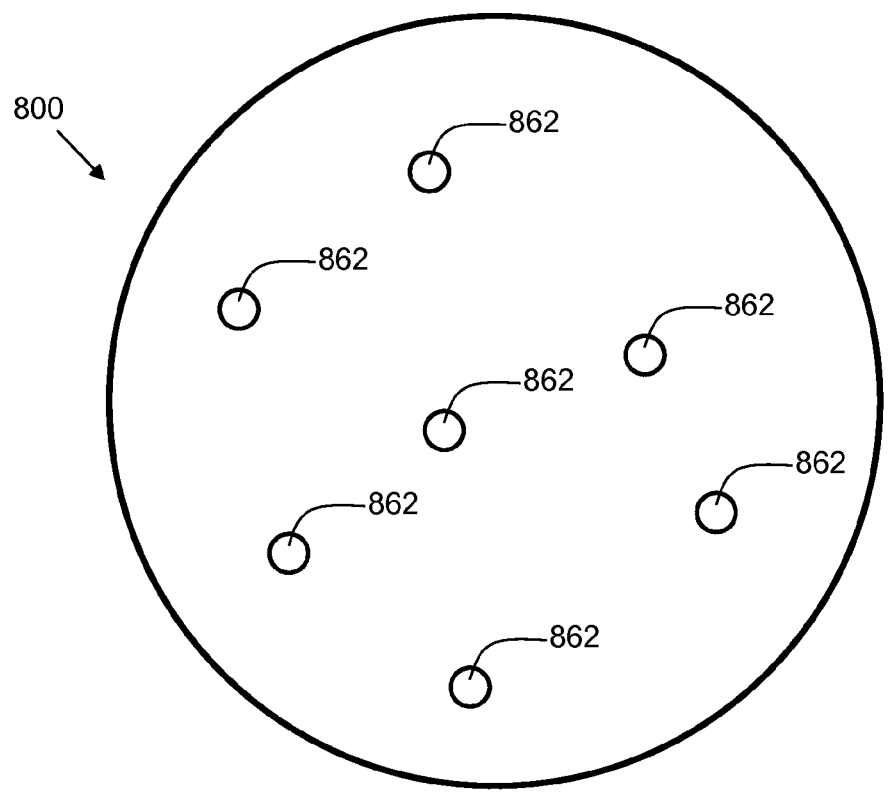

FIG. 8 shows an exemplary substrate with various measurement locations.

Figure 9:
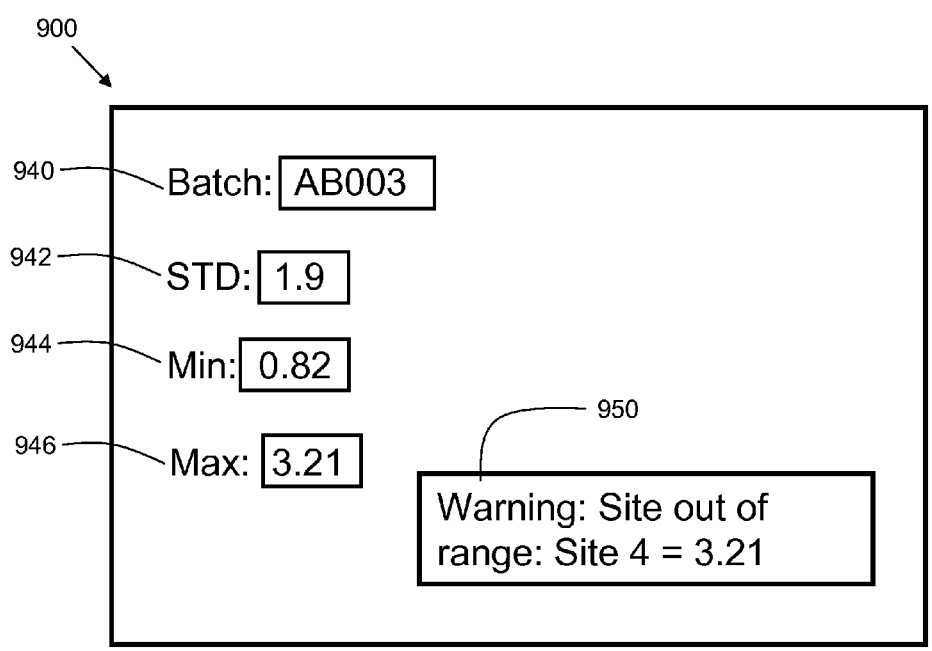

FIG. 9 shows an exemplary display in accordance with alternative embodiments of the present invention.

DETAILED DESCRIPTION

Embodiments of the present invention provide systems and methods for performing X-ray Photoelectron Spectroscopy (XPS) measurements in a semiconductor environment. A reference element peak is selected and tracked as part of the measurement process. Peak shift of the reference element peak, in electron volts (eV) is tracked and applied to other portions of acquired spectrum to compensate for the shift, which results from surface charge fluctuation.

FIG. 1A is a block diagram of a system 100 in accordance with embodiments of the present invention. System 100 comprises an X-ray source 130 which is configured and disposed to irradiate a semiconductor substrate 134 with X-rays X. In some embodiments, X-ray source 130 comprises an aluminum anode, producing a Kα X-ray line with a photon energy of 1486.6 eV. In other embodiments, X-ray source 130 comprises a magnesium anode, producing a Kα X-ray line with a photon energy of 1253.6 eV. In some embodiments, X-ray source 130 is a multi-energy X-ray source, and may comprise both an aluminum anode and a magnesium anode. Substrate 134 is placed on sample stage 136, and may represent a processed wafer at certain stages of the fabrication process. Electrons e are emitted from the semiconductor substrate 134 and are detected by detector 133. The detector 133, X-ray source 130, and substrate 134 may be contained within an ultra high vacuum (UHV) chamber 138.

XPS computer 118 comprises memory 120, and a processor 122 which is configured to read and write memory 120. The memory 120 may be a non-transitory computer-readable medium, such as flash, ROM, non-volatile static ram, or the like. The non-transitory memory 120 contains instructions that, when executed by processor 122, control the various subsystems to operate system 100. XPS computer 118 may also include a display 124 and a user interface 126 for interacting with the system 100. The user interface 126 may include a keyboard, touch screen, mouse, or the like. XPS computer 118 further comprises a plurality of input and output interfaces (I/O) 123 to interface with the detector (e.g., to receive counts of electrons and generate spectra), control the X-ray source (e.g., activation and deactivation of the X-ray source), and optionally, control position of the sample stage 136.

FIG. 1B is a top-down view of the semiconductor substrate 134 indicating a target area T, which is region where the X-rays X are incident on the substrate 134. In some embodiments, the target area is circular and has a diameter ranging from about 20 micrometers to about 30 micrometers. In some embodiments, sample stage 136 may be a movable sample stage, movable in the X direction 140 and Y direction 142. The XPS computer 118 may be configured and disposed to locate sample stage 136 to a desired position such that the target area T is irradiating the desired area of semiconductor substrate 134 for a measurement. In general, XPS is a surface measurement technique, and may be used to analyze films and film layer stacks to a depth of about 100 angstroms. In some embodiments, the semiconductor substrate 134 is irradiated with X-ray energy for a duration ranging from 1 second to 120 seconds. In other embodiments, the semiconductor substrate 134 is irradiated with X-ray energy for a duration ranging from 120 seconds to 600 seconds.

FIG. 2 is a graph 200 of an exemplary XPS reference element peak 228. The X-axis represents energy, in electron-volts (eV). The Y-axis 232 represents the counts of electrons detected at a given energy. The curve (spectrum) 226 represents the counts as a function of binding energy. In general, for a single element energy line, the curve 226 renders with a peak 228. An element window W may be defined with a upper limit 222 and lower limit 224. In some embodiments, the element window W may be based on the full-width half maximum (FWHM) value of a reference peak. In some embodiments, peak widths (FWHM) may range between 0.4-1.2 eV for various pure elements and some compounds. Electrons detected with an energy level between upper limit 222 and lower limit 224 may be considered as representative of the presence of a particular element. Hence, by defining windows and counting detected electrons having an energy level within those windows, the constituents of a sample, such as a semiconductor substrate may be identified and measured. In accordance with embodiments of the present invention, a reference element peak is selected. In some embodiments, oxygen is used as the reference element peak. However, other elements may be used, including, but not limited to, nitrogen and silicon. In some embodiments, selection of the reference peak may be performed in an automated manner. Before each measurement, a pre-scan measurement may be performed. A pre-scan measurement is a special purpose measurement that may be performed prior to the analytical measurement (the measurement used to identify constituents and assays). After the pre-scan, a reference peak may be selected by identifying the tallest peak (the maximum amplitude of the spectrum), which yields the strongest, most pronounced signal for reliable tracking in a relatively short testing time.

FIG. 3A shows an exemplary pre-scan spectrum 300. In some embodiments, a first energy range may be selected for the pre-scan, and a second energy range selected for the analytical measurement. In some embodiments, the selected energy range for the analytical measurement may be in the range of 30 to 40 eV. In some embodiments, the energy range for the pre-scan is two to three times larger than the energy range for the analytical measurements. In FIG. 3A, the energy range (from one end of the X-axis 330 to the other) is 200 eV. In some embodiments, a sufficient resolution may be achieved with a wide energy range, such that both the identification of a reference peak and an analytical measurement may be performed in the same measurement, without performing a pre-scan. As shown in FIG. 3A, the energy range on the X-axis 330 is from 0 to 1000 eV, which is wider than the energy range of FIG. 2 (510 eV to 550 eV). Increasing the energy range can be beneficial for identifying a good candidate for a reference element peak. Peak 332 is a peak of maximum amplitude within spectrum 300, and hence, is a good candidate for the reference element peak.

FIG. 3B shows a wide range scan, with an energy range of 1000 eV along X-axis 331. Peak 343 is a peak of maximum amplitude within spectrum 300, and hence, is a good candidate for the reference element peak. In some embodiments, a wide range scan may be used when analyzing a material for the first time, to identify a good candidate for the reference element peak.

FIG. 4 is a graph 400 illustrating reference element peak shift D. As X-rays irradiate a sample, such as a semiconductor substrate (wafer), the wafer builds up surface charge. This may occur even with attempts to ground the wafer. The surface charge skews the location of the peaks. Embodiments of the present invention periodically or continually monitor the position of the reference element peak and compute the amount of shift along the X-axis 430. Embodiments of the present invention then apply a correction to a plurality of element windows, based on the computed shift D.

FIG. 5 is a graph 500 of an exemplary XPS measurement peak, indicating shift. Initial measurement spectrum 526 has peak position 529, which is an initial location, and a second measurement spectrum 527 of the same sample has peak position 531, which is a subsequent location. A shift D represents the energy shift between the initial measurement and the second measurement, largely due to fluctuation of surface charge of the semiconductor substrate that is being measured. For a given sample (e.g. semiconductor substrate), the shift D is proportional across energy ranges. Hence, by tracking the position of a reference element peak, such as an oxygen peak, changes in position may be applied to other energy levels. For example, the peaks shown in FIG. 4 are in the range of about 170 eV, and may be indicative of the presence of a material such as sulfur (using the 2p spectral line). In this example, by tracking the oxygen peak, which may be in the range of about 532 eV (using the 1s spectral line), a corresponding correction is made to the element window defined for sulfur, such that the sulfur window lines up with the sulfur peak as surface charge fluctuates on the semiconductor substrate during a measurement. In alternative embodiments, instead of adjusting X position (energy limits) of the element windows, the spectrum X-scale may be shifted to match the reference energy.

FIG. 6 is a flowchart 600 indicating process steps for embodiments of the present invention. In process step 650, a sample is irradiated with X-rays. In process step 652, emitted electrons are detected, and a measurement spectrum is acquired. In process step 654, a reference element peak is selected. The selection process may comprise performing a pre-scan at a wider energy range to identify the peak of maximum amplitude within the spectrum. In some embodiments, the reference element peak may comprise an oxygen peak, silicon peak, or nitrogen peak. In process step 656, the initial peak location is recorded. In particular, the X-axis location of the peak, which represents the energy level, in eV of the peak, is recorded. In process step 658, the reference element peak is periodically or continuously tracked. In process step 660, a shift is computed as the peak is tracked. In process step 662, the correction is dynamically applied to the measurement results. The correction may comprise adjusting upper and lower limits of predefined element windows, and/or shifting the spectrum X-scale to match the reference energy In process step 664, results may be displayed (e.g. on display 124 of FIG. 1). The results may include a list of constituents and their concentrations. In some embodiments, film thicknesses may also be displayed.

FIG. 7 shows an exemplary display 700 in accordance with embodiments of the present invention. In some embodiments, a predetermined list of constituents and corresponding predetermined limits of the concentrations for each of the constituents may be established. In the example of FIG. 7, four constituents are shown: Si (742), Cl (744), As (746), and Ni (748). A warning 750 may be presented if a concentration of one or more constituents of the semiconductor substrate are outside of the predetermined limits. In the example shown, a warning is generated because the nickel reading (0.74%) is higher than the predefined limits specified for this material (0.5%-0.65%). In some embodiments, other units of measure, such as parts-per-million (ppm) may be used instead of, or in addition to percentages. The material may be referenced by a batch identifier 740, or other suitable identifier. Thus, for a given material, embodiments of the present invention can perform quality checks to identify issues where one or more constituents are outside specified ranges. When implemented as an inline measurement system, embodiments of the present invention can serve to improve quality and product yield by detecting problems as early as possible in the fabrication process, for example, after blanket deposition of various films. In some cases, the amount of various elements in a compound is critical for proper operation of an integrated circuit. Therefore, accurate measurement is essential to achieve acceptable product quality and yield. Embodiments of the present invention overcome shortcomings of prior art XPS systems caused by fluctuating surface charge. Hence, embodiments of the present invention serve to improve the accuracy of XPS measurements, and thus, serve to improve overall semiconductor quality.

FIG. 8 shows an exemplary substrate (wafer) 800 with various measurement locations 862. Embodiments of the present invention make multiple measurements of a single wafer. For a patterned wafer, the measurement tool may move to various chips within the wafer to perform a measurement. For blanket wafers (non-patterned) that are encountered earlier in the fabrication process, various locations (sites) within the wafer may be measured. In some embodiments, the eV shift detected using the reference element peak is recorded at each site or location measured on a wafer, and a standard deviation computed. If the standard deviation exceeds a predetermined value, or if one or more measurements are outside the standard deviation by a predetermined value, a warning may be presented to the user. The warning indicates that the charge fluctuation may not be constant across the wafer, and may warrant further inspection to determine if the fabrication process is within specified limits.

FIG. 9 shows an exemplary display 900 in accordance with alternative embodiments of the present invention. The material being measured may be referenced by a wafer identifier 940, or other suitable identifier. Information about the various measurements performed on the wafer may be displayed. Standard deviation field 942 shows the standard deviation of the shift in eV required at each location (site) that is measured. Minimum field 944 shows the minimum amount of shift required at a given location. Maximum field 946 shows the maximum amount of shift required at a given location. Warning field 950 may present a warning if a predetermined threshold is exceeded. In some embodiments, the warning may be presented if the standard deviation exceeds a predetermined value, or a maximum amount of shift exceeds a predetermined value. In the case where a maximum amount of shift exceeds a predetermined value, the measurement location on the wafer may also be presented. In this way, process engineers can examine the particular wafer and location to confirm if any process issues exist at that location on the wafer. Hence, the outlier behavior in terms of the amount of charge fluctuation may be indicative of a process issue at the corresponding location on the wafer.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, circuits, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A method for performing measurements with an X-ray photoelectron spectroscopy measurement tool, comprising:
   irradiating a semiconductor substrate with X-ray energy;
   detecting emitted electrons from the semiconductor substrate;
   selecting a reference element peak based on the detected emitted electrons;
   recording an initial location for the reference element peak;
   computing a shift in location for the reference element peak; and applying a correction to a plurality of element windows, based on the computed shift; and
   further comprising performing a measurement at multiple locations on the semiconductor substrate, and further comprising computing a standard deviation of shift for the multiple reference element peak locations.

2. The method of claim 1, wherein selecting a reference element peak based on the detected emitted electrons comprises identifying a peak of maximum amplitude within a spectrum.

3. The method of claim 2, wherein selecting a reference element peak further comprises performing a pre-scan measurement at a first energy range, and performing an analytical measurement at a second energy range.

4. The method of claim 1, wherein irradiating a semiconductor substrate with X-ray energy comprises irradiating a semiconductor substrate with X-ray energy for a duration ranging from 1 second to 120 seconds.

5. The method of claim 1, further comprising computing a maximum shift value and corresponding location.

6. The method of claim 5, further comprising:
recording a predetermined limit for the standard deviation of shift for a plurality of locations; and
presenting a warning if the standard deviation of shift exceeds the predetermined limit.

7. The method of claim 6, further comprising:
recording a predetermined limit for the maximum shift value for the semiconductor substrate; and
presenting a warning if the maximum shift value exceeds the predetermined limit.

8. The method of claim 1, further comprising:
receiving predetermined limits for one or more constituents of the semiconductor substrate; and
presenting a warning if a concentration of one or more constituents of the semiconductor substrate are outside of the predetermined limits.

9. A system for performing measurements with an X-ray photoelectron spectroscopy measurement tool, comprising:
an X-ray source configured and disposed to irradiate a semiconductor substrate;
a detector configured to detect emitted electrons from the semiconductor substrate;
a processor, configured and disposed to access a non-transitory memory, wherein the non-transitory memory contains instructions, that when executed by the processor, perform the steps of:
selecting a reference element peak based on the emitted electrons;
recording an initial location for the reference element peak;
computing a shift in location for the reference element peak; and
applying a correction to a plurality of element windows, based on the computed shift; and
performing a measurement at multiple locations on the semiconductor substrate;
computing a standard deviation of shift for the multiple reference element peak locations;
recording a predetermined limit for the standard deviation of shift; and
presenting a warning if the standard deviation of shift exceeds the predetermined limit.

10. The system of claim 9, wherein the non-transitory memory contains instructions, that when executed by the processor, perform the steps of:
recording a predetermined limit for a maximum shift value for the semiconductor substrate; and
presenting a warning if the maximum shift value exceeds the predetermined limit.

11. The system of claim 9, wherein the non-transitory memory contains instructions, that when executed by the processor, perform the steps of:
receiving predetermined limits for one or more constituents of the semiconductor substrate; and
presenting a warning if a concentration of one or more constituents of the semiconductor substrate are outside of the predetermined limits.

12. A non-transitory computer-readable medium comprising:
instructions, which when executed by a processor, perform the steps of:
irradiating a semiconductor substrate with X-ray energy;
detecting emitted electrons from the semiconductor substrate;
selecting a reference element peak based on the detected emitted electrons;
recording an initial location for the reference element peak;
computing a shift in location for the reference element peak; and
applying a correction to a plurality of element windows, based on the computed shift; and
instructions, which when executed by a processor, perform the steps of:
performing a measurement at multiple locations on the semiconductor substrate;
recording a predetermined limit for a standard deviation of shift for a plurality of reference element peak locations; and
presenting a warning if the standard deviation of shift exceeds the predetermined limit.

13. The non-transitory computer-readable medium of claim 12, further comprising:
instructions, which when executed by a processor, perform the step of identifying a peak of maximum amplitude within a spectrum.

14. The non-transitory computer-readable medium of claim 13, further comprising:
instructions, which when executed by a processor, perform a pre-scan measurement at a first energy range and an analytical measurement at a second energy range.

15. The non-transitory computer-readable medium of claim 12, further comprising:
instructions, which when executed by a processor, perform the step of irradiating a semiconductor substrate with X-ray energy for a duration ranging from 120 seconds to 600 seconds.

16. The non-transitory computer-readable medium of claim 12, further comprising: instructions, which when executed by a processor, perform the steps of:
recording predetermined limits for one or more constituents of the semiconductor substrate; and
presenting a warning if a concentration of one or more constituents of the semiconductor substrate are outside of the predetermined limits.

* * * * *